United States Patent
Hirai et al.

(10) Patent No.: US 9,651,475 B2
(45) Date of Patent: May 16, 2017

(54) OPTICAL SENSOR APPARATUS AND METHOD OF PRODUCING OPTICAL ELEMENT USED IN OPTICAL SENSOR APPARATUS

(71) Applicant: Panasonic Intellectual Property Management Co., Ltd., Osaka (JP)

(72) Inventors: Takahiko Hirai, Osaka (JP); Kazuki Yamaguchi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/444,000

(22) PCT Filed: Nov. 27, 2013

(86) PCT No.: PCT/JP2013/006974
§ 371 (c)(1),
(2) Date: May 19, 2015

(87) PCT Pub. No.: WO2014/083847
PCT Pub. Date: Jun. 5, 2014

(65) Prior Publication Data
US 2015/0316466 A1 Nov. 5, 2015

(30) Foreign Application Priority Data
Nov. 30, 2012 (JP) .................................. 2012-263279

(51) Int. Cl.
G01N 21/09 (2006.01)
G01N 21/3504 (2014.01)
(Continued)

(52) U.S. Cl.
CPC ............ G01N 21/09 (2013.01); C23C 14/081 (2013.01); C23C 14/14 (2013.01); C23C 16/06 (2013.01);
(Continued)

(58) Field of Classification Search
CPC ............... G01N 21/09; G01N 21/3504; G01N 2201/0873
See application file for complete search history.

(56) References Cited

U.S. PATENT DOCUMENTS

| 4,795,253 A | 1/1989 | Sandridge et al. |
| 4,823,168 A | 4/1989 | Kamahori et al. |

(Continued)

FOREIGN PATENT DOCUMENTS

| CN | 1056159 A | 11/1991 |
| CN | 102183482 A | 9/2011 |

(Continued)

OTHER PUBLICATIONS

Extended European Search Report issued in European Application No. 13857877.8 dated Sep. 25, 2015.
(Continued)

*Primary Examiner* — David Porta
*Assistant Examiner* — Faye Boosalis
(74) *Attorney, Agent, or Firm* — McDermott Will & Emery LLP (57) ABSTRACT

An optical sensor apparatus includes a light receiving element configured to produce an output according to a light receiving state, and an optical element including a reflecting layer including a metal film, and being arranged such that at least some of incident light on the light receiving element is light that is reflected by the reflecting layer. The optical element further includes a corrosion resistant layer for suppressing corrosion of the reflecting layer, and the reflecting layer includes a surface covered by the corrosion resistant layer formed by vapor plating.

9 Claims, 5 Drawing Sheets

(51) Int. Cl.
*C23C 14/08* (2006.01)
*C23C 14/14* (2006.01)
*C23C 16/06* (2006.01)
*C23C 16/40* (2006.01)

(52) U.S. Cl.
CPC ....... *C23C 16/403* (2013.01); *G01N 21/3504* (2013.01); *G01N 2201/0873* (2013.01)

(56) References Cited

U.S. PATENT DOCUMENTS

| | | | |
|---|---|---|---|
| 5,510,895 | A | 4/1996 | Sahagen |
| 6,486,474 | B1 | 11/2002 | Owen et al. |
| 2014/0070101 | A1 | 3/2014 | Matsushima et al. |

FOREIGN PATENT DOCUMENTS

| | | |
|---|---|---|
| DE | 4002631 A1 | 8/1991 |
| EP | 0266769 A2 | 5/1988 |
| GB | 1559503 A | 1/1980 |
| JP | 64-78134 A | 3/1989 |
| JP | 3-101451 U | 10/1991 |
| JP | 8-510829 A | 11/1996 |
| JP | 2005-143943 A | 6/2005 |
| JP | 2005-164303 A | 6/2005 |
| JP | 2012-220351 A | 11/2012 |
| WO | 94/20013 A1 | 9/1994 |

OTHER PUBLICATIONS

International Search Report and Written Opinion, issued in corresponding International Patent Application No. PCT/JP2013/006974, mailed on Feb. 10, 2014; 10 pages with English translation of the Search Report.

First Office Action issued in corresponding Chinese Patent Application No. 201380060256.5, mailed on Aug. 18, 2016; with English translation.

OPTICAL SENSOR APPARATUS AND METHOD OF PRODUCING OPTICAL ELEMENT USED IN OPTICAL SENSOR APPARATUS

RELATED APPLICATIONS

This application is the U.S. National Phase under 35 U.S.C. §371 of International Patent Application No. PCT/JP2013/006974, filed on Nov. 27, 2013, which in turn claims the benefit of Japanese Application No. 2012-263279, filed on Nov. 30, 2012, the disclosures of which Applications are incorporated by reference herein.

TECHNICAL FIELD

This invention relates to an optical sensor apparatus including a light receiving element and an optical element including a reflecting layer, and a method of producing the optical element used in the optical sensor apparatus.

BACKGROUND ART

Heretofore, a gas detector, a human sensor, and the like have been known as optical sensor apparatuses including a light receiving element and an optical element including a reflecting layer. For example, a gas sensor described in JP 2012-220351 A (hereinafter referred to as "Document 1") has a configuration in which a space for introducing a detection target gas is formed between a light emitting element (light emitting unit) and a light receiving element (light receiving unit), and a light guide body is arranged between the light emitting element and the light receiving element. The inside of the light guide body includes a reflecting layer (reflecting mirror) formed by a metal such as aluminum. The reflecting mirror described in Document 1 is formed by a metal plate or a metal film. The gas sensor can detect gas concentration by utilizing the fact that the gas introduced in the light guide body absorbs light having a specific wavelength.

A corrosive gas may be introduced inside the gas sensor of this type depending on the use environment. For example, if the gas sensor is used in a kitchen, sulfide and chloride may possibly be introduced inside the light guide body. Accordingly, there is concern that the reflecting layer formed by a metal will be corroded, resulting in sensitivity reduction in gas detection due to reduction of reflectance.

It is considered that a corrosion resistant layer (corrosion protective covering) is formed on a surface of the reflecting layer in order to suppress corrosion of the reflecting layer (refer to JP 2005-143943 (hereinafter referred to as "Document 2"), for example). A corrosion protective covering made of a synthetic resin is disclosed in Document 2.

As described above, although it is effective to cover the surface of the reflecting layer with the corrosion resistant layer in order to suppress corrosion of the reflecting layer, there is a problem in that time required for production is prolonged since drying after application of the synthetic resin is required in the case where the corrosion resistant layer is formed by application of the synthetic resin. Also, since a solvent evaporates when the synthetic resin is dried, film thickness control of the reflecting layer becomes difficult, and bubbles are mixed in accompanying evaporation of the solvent, resulting in possible yield reduction.

SUMMARY OF INVENTION

The present invention has been made in view of the above-described problems, and an object of the present invention is to provide an optical sensor apparatus in which time required for producing an optical element including a reflecting layer can be reduced, control of film thickness is relatively easy, and yield improvement can be expected, and furthermore is to provide a method of producing the optical element used in the optical sensor apparatus.

The optical sensor apparatus according to the present invention includes: a light receiving element configured to produce an output according to a light receiving state; and an optical element including a reflecting layer including a metal film, and being arranged such that at least some of incident light on the light receiving element is light that is reflected by the reflecting layer. The optical element further includes a corrosion resistant layer for suppressing corrosion of the reflecting layer, and the reflecting layer includes a surface covered by the corrosion resistant layer formed by vapor plating.

It is preferable that the optical sensor apparatus further includes a light emitting element with an emission wavelength that is in a predetermined wavelength region, the light receiving element is configured such that a received light intensity with respect to a specific wavelength determined by a type of a detection target gas among the wavelength region is reflected in an output value, and the optical element is arranged such that an optical path between the light emitting element and the light receiving element is formed in a monitoring space into which the detection target gas is introduced.

It is preferable that, in the optical sensor apparatus, the optical element is tubular, and includes a tube wall having an air hole passing through the tube wall and an inner surface on which the reflecting layer is disposed, the light emitting element is coupled to one end portion of the optical element in a specific direction in which opening surfaces of two end portions of the optical element oppose each other, the light receiving element is coupled to another end portion of the optical element in the specific direction, and the optical element is configured to guide light between the light emitting element and the light receiving element.

It is preferable that, in the optical sensor apparatus, the corrosion resistant layer has a film thickness of 100 nm or more.

It is preferable that, in the optical sensor apparatus, incident light on the light receiving element is light in an infrared region, and the reflecting layer is formed by Al, and the corrosion resistant layer is formed by $Al_2O_3$.

A method of producing an optical element used in the optical sensor apparatus includes: forming the reflecting layer by forming Al film in a gas phase on a target surface of a base material of the optical element; and forming the corrosion resistant layer including $Al_2O_3$ in a gas phase on a surface of the reflecting layer after forming the reflecting layer.

It is preferable that, in the method of producing the optical element used in the optical sensor apparatus, film formation of the reflecting layer and film formation of the corrosion resistant layer are performed in a same space, and the film formation of the reflecting layer is performed in a vacuum atmosphere, and the film formation of the corrosion resistant layer is performed in an oxidizing atmosphere in which oxygen is introduced.

According to the configuration of the present invention, drying of the corrosion resistant layer as in the case where a synthetic resin is applied to the reflecting layer as the corrosion resistant layer is not required since the corrosion resistant layer is formed by vapor plating, and as a result the time required for producing the optical element including the reflecting layer can be reduced. Moreover, there is an advantage that yield improvement can be expected since the film thickness control is relatively easy, and a bubble is not generated in the corrosion resistant layer.

BRIEF DESCRIPTION OF DRAWINGS

Preferred embodiments of the present invention will now be described in further details. Other features and advantages of the present invention will become better understood with regard to the following detailed description and accompanying drawings where.

DESCRIPTION OF EMBODIMENTS

Although the present embodiment will be described using a gas sensor as an example, the technique described using the following embodiment can be used in other configurations as long as the optical sensor apparatus uses an optical element including a reflecting layer in combination with a light receiving element. For example, in the case where a mirror is used as an optical element for determining a field of view in a human sensor serving as an optical sensor apparatus, in which a pyroelectric infrared sensor is used as a light receiving element, the technique described in the present embodiment can be adopted. Also, in the case where a mirror is used as an optical element for setting an optical path in an optical sensor apparatus for detecting a passerby or smoke that blocks the optical path formed between a light emitting element and a light receiving element, the technique described in the present embodiment can be adopted.

Figure 1A:
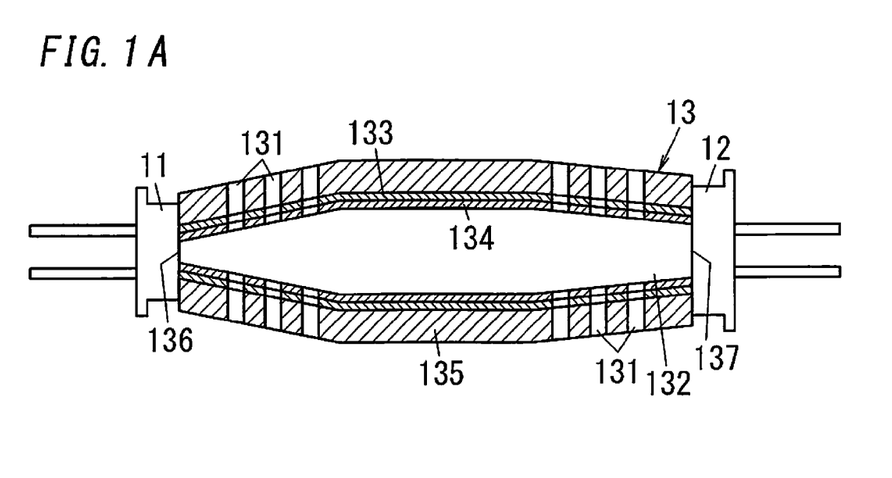
FIG. 1A is a cross-sectional view illustrating a gas sensor according to an embodiment.
Figure 1B:
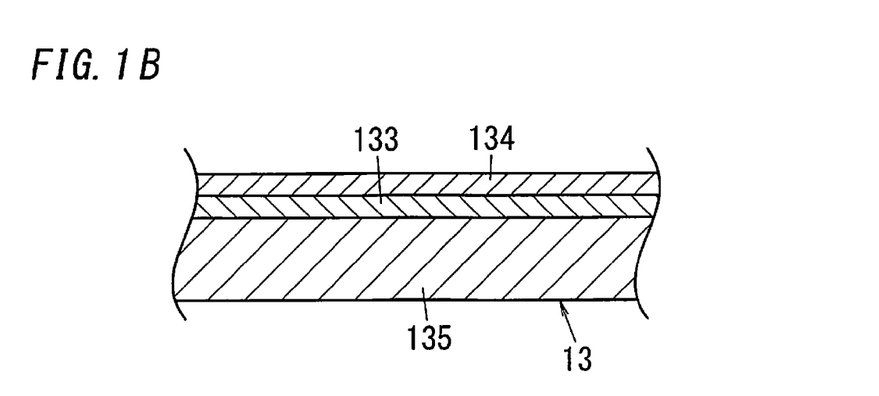
FIG. 1B is a cross-sectional view illustrating main portions of the gas sensor according to the embodiment.
Figure 2:
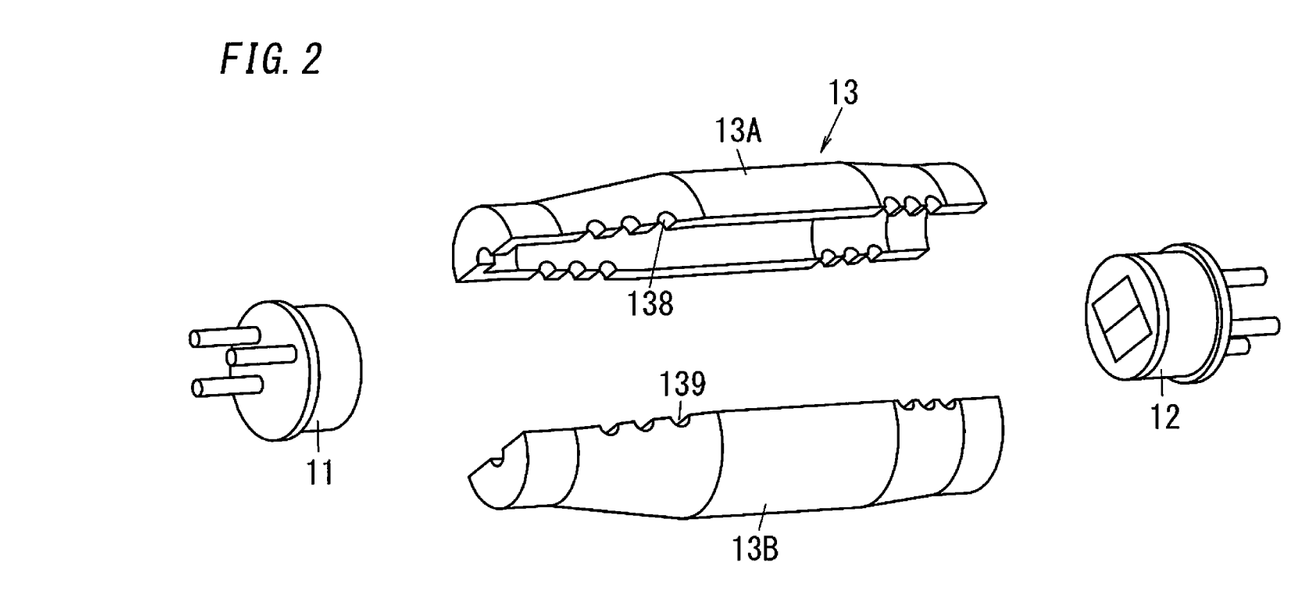
FIG. 2 is an exploded perspective view illustrating the gas sensor according to the embodiment.

The gas sensor includes a light emitting element 11, a light receiving element 12, and an optical element 13, as shown in FIGS. 1A, 1B, and 2. Although a fitting member interposed between the optical element 13 and the light emitting element 11 and a fitting member between the optical element 13 and the light receiving element 12 are required in order to couple the light emitting element 11 and the light receiving element 12 to the optical element 13, the fitting members will not be described in detail in the present embodiment.

A light emitting diode, a laser diode, an OLED (Organic Light Emitting Diode), and the like are known as typical examples of the light emitting element 11. A photodiode, a phototransistor, a pyroelectric infrared sensor, a CCD (Charge Coupled Device) image sensor, a CMOS (Complementary Metal Oxide Semiconductor) image sensor, and the like are known as typical examples of the light receiving element 12. The illustrated examples of the light emitting element 11 and the light receiving element 12 are examples, and the light emitting element 11 and the light receiving element 12 are not limited thereto.

The optical element 13 is a synthetic resin molded article and is formed in a tubular shape, and a plurality of air holes 131 are formed in a tube wall of the optical element 13 so as to pass through the tube wall. Also, the optical element 13 is formed by coupling a pair of half-split bodies 13A and 13B. The half-split bodies 13A and 13B are members, which form a pair, that are split by a plane including a center line along a specific direction in which opening surfaces 136 and 137 of two end portions of the optical element 13 oppose each other, that is, the center line of the optical element 13. The half-split bodies 13A and 13B are coupled by a technique selected from coupling by fitting, ultrasonic welding, adhesion, and the like. Each of the pair of half-split bodies 13A and 13B may be configured by a single member, as shown in FIG. 2, or may be configured by two or more members. In the optical element 13 of the present embodiment, the specific direction is a longitudinal direction of the optical element 13.

The optical element 13 is formed in a shape in which a central portion of an outer surface thereof in the specific direction bulges compared with the two end portions. A light guide hole 132 that passes through in the specific direction of the optical element 13 is formed in a shape in which the diameter thereof is at the maximum in the central portion in the specific direction and smaller in the two end portions than the central portion. Furthermore, the light guide hole 132 is formed in a shape in which the diameter thereof in one end portion (opening surface 136) to which the light emitting element 11 is coupled is smaller than the diameter in the other end portion (opening surface 137) to which the light receiving element 12 is coupled. An inner surface of the optical element 13 is formed in a shape in which the central portion thereof in the specific direction of the optical element 13 bulges compared with the two end portions, similarly to the outer surface of the optical element 13, and has a smoothly curved shape.

Each of the pair of half-split bodies 13A and 13B of the optical element 13 includes a base material 135, a reflecting layer 133 including a metal film covering substantially the entirety of an inner surface of the base material 135, and a corrosion resistant layer 134 covering the entirety of the reflecting layer 133. A material having high reflectance with respect to a wavelength of light that is transmitted and received between the light emitting element 11 and the light receiving element 12 is selected for the reflecting layer 133, and a material having transparency with respect to a wavelength of light that the light receiving element 12 focuses on is selected for the corrosion resistant layer 134. Specific examples of the material and the film thickness of the reflecting layer 133 and the corrosion resistant layer 134 will be described later.

In the optical element 13, with the configuration described above, gas flows into the light guide hole 132 through the air holes 131. Since the light absorptivity of the gas has wavelength dependence according to the type of the gas, by selecting the wavelength of light that is transmitted and received between the light emitting element 11 and the light receiving element 12, the concentration of the detection target gas can be obtained based on the light intensity received by the light receiving element 12.

For example, when a ratio of received light intensities with respect to two types of light (wavelength) is obtained using two types of light having wavelengths that are different from each other, one of the two types of light being absorbed by the detection target gas, and the other not being absorbed by the gas, the concentration of the detection target gas can be expressed in a form including the ratio as a parameter. That is, the relationship between the gas concentration and the ratio of the received light intensities can be expressed in a form of a function or a data table.

For example, carbon dioxide is assumed to be the detection target. In this case, the light receiving element 12 is configured such that the output value therefrom reflects a received light intensity in a specific wavelength band centered at a wavelength of light that is absorbed by carbon dioxide, namely 4.3 μm, and a received light intensity in a specific wavelength band centered at a wavelength of light that is not absorbed by carbon dioxide, namely 3.9 μm, for example. The light receiving element 12 of this configuration can be realized by combining two narrowband band-pass filters that select respective wavelength bands and pass light in the selected respective wavelength bands, and two infrared sensors that each receive light that has passed each band-pass filter.

Also, the light emitting element 11 may emit light in a predetermined wavelength region including light in the specific wavelength bands received by the light receiving element 12. That is, in the example described above, the light emitting element 11 may be configured to emit light in an infrared region including a wavelength region from 3.9 to 4.3 μm. A heater having good responsiveness that is microfabricated by MEMS (Micro Electro Mechanical Systems) technology can be adopted as this type of light emitting element 11, in addition to an infrared-emitting diode, for example.

In the gas sensor of this configuration, the light emitting element 11 emits light intermittently, and the light emitted from the light emitting element 11 is guided inside the optical element 13 and reaches the light receiving element 12. While the light is guided from the light emitting element 11 to the light receiving element 12, some of light that is emitted from the light emitting element 11 is reflected by the reflecting layer 133 and enters the light receiving element 12. An inner surface of the optical element 13 smoothly curves so as to reflect light in various angles, and causes the light emitted from the light emitting element 11 to fill an internal space of the light guide hole 132.

That is to say, light in the infrared region that is emitted from the light emitting element 11 spreads out over the entire internal space of the optical element 13 without being absorbed by the tube wall of the optical element 13, and is guided toward the light receiving element 12. Accordingly, the ratio of light that is incident on the light receiving element 12 relative to the light that is emitted from the light emitting element 11 increases, and an optical path length also relatively lengthens. As a result, existence of gas inside the optical element 13 can be easily detected.

In the case where the detection target gas is introduced in the internal space of the optical element 13 through the air holes 131, the light having the specific wavelength emitted from the light emitting element 11 is absorbed by the gas with absorbance according to the gas concentration. Accordingly, in the light receiving element 12, an output value (first output value) with respect to the specific wavelength band decreases compared with the case where the detection target gas does not exist. On the other hand, since the output value (second output value) with respect to the specific wavelength band of light that is not absorbed by the detection target gas ideally does not change from the case where the detection target gas does not exist, the gas concentration can be known from the ratio of the two output values (first output value/second output value, for example).

According to the configuration described above, the internal space (light guide hole 132) of the optical element 13 functions as a monitoring space to which the detection target gas is introduced, and the light from the light emitting element 11 passes through the monitoring space. Since an optical path between the light emitting element 11 and the light receiving element 12 is formed like a mesh in the monitoring space by the reflecting layer 133 that is formed on substantially the entire inner surface of the optical element 13, the light can be caused to pass through the gas even in a case where the detection target gas is localized in the monitoring space.

Incidentally, in the above-described gas sensor, not only the detection target gas, but also a corrosive gas including sulfur, chlorine, nitrogen, or the like enters the optical element 13, depending on the use environment. Since the reflecting layer 133 is formed by a metal film in order to obtain high reflectance, the reflecting layer 133 corrodes due to the corrosive gas depending on the type of metal forming the reflecting layer 133, and the performance of the gas sensor deteriorates over time.

When selecting a metal used for the reflecting layer 133, the cost thereof needs to be considered in addition to, obviously, having high reflectance with respect to the specific wavelength detected by the light receiving element 12. Accordingly, gold (Au), which has a good reflectance characteristic but is expensive, is difficult to adopt considering the merchandise cost. Moreover, in many cases where Au is used, nickel (Ni) is used as the substrate for increasing the bonding strength. When one or more pinholes are formed in an Au layer, water attaches to the pinholes, and a sulphurous acid gas or the like comes in contact therewith, corrosion can be accelerated due to a local battery formed by Au and Ni.

On the other hand, although silver (Ag) has good reflectance and is not expensive compared with Au, it is likely to be corroded by a corrosive gas including sulfur. Although aluminum (Al) and chromium (Cr) have good reflectance and are not expensive compared with Au, they have a property in which reflectance is lowered due to oxidation. Therefore, although Ag, Al, and Cr are candidates for the material of the reflecting layer 133, they cannot be used alone.

Furthermore, since the reflecting layer 133 is fixed to the base material 135 made of a synthetic resin molded article that forms the optical element 13, the reflecting layer 133 needs to be easily joined to the base material 135, in addition to the above conditions. Also, depending on the type of metal, the reflectance of the reflecting layer 133 may have wavelength dependence, and not satisfy a criterion of reflectance (reflectance of 90% or more, for example) in the wavelength region corresponding to the detection target gas.

A material that satisfies the conditions that formation is easy, substrate treatment for fixing the reflecting layer 133 is easy, resistance to heat is high, and cost is low, is selected as the base material 135 of the optical element 13. For example, a nylon-based synthetic resin, polyphenylene sulfide, polybutylene terephthalate, or the like can be selected as this type of material.

Formation of a base layer including $SiO_2$ on a surface of the base material 135 as a substrate treatment is conceivable, in order to adhere the reflecting layer 133 to the base material 135. However, there is a problem in that process steps increase if the base layer made of a material that is different from the reflecting layer 133 is formed on the base material 135, in addition to the reflecting layer 133 and the corrosion resistant layer 134.

Therefore, in the present embodiment, a plasma treatment is performed in a nitrogen atmosphere. By performing the plasma treatment on the surface of the base material 135, the surface of the base material 135 is cleaned, and the adhesiveness of the reflecting layer 133 increases.

The surface of the reflecting layer 133 is covered with the corrosion resistant layer 134, as described above. A material that is not corroded with an assumed corrosive gas and passes light in the wavelength region detected by the light receiving element 12 is selected for the corrosion resistant layer 134. Aluminum oxide ($Al_2O_3$), a silicate glass, diamond, or the like can be selected as this type of material.

Figure 3:
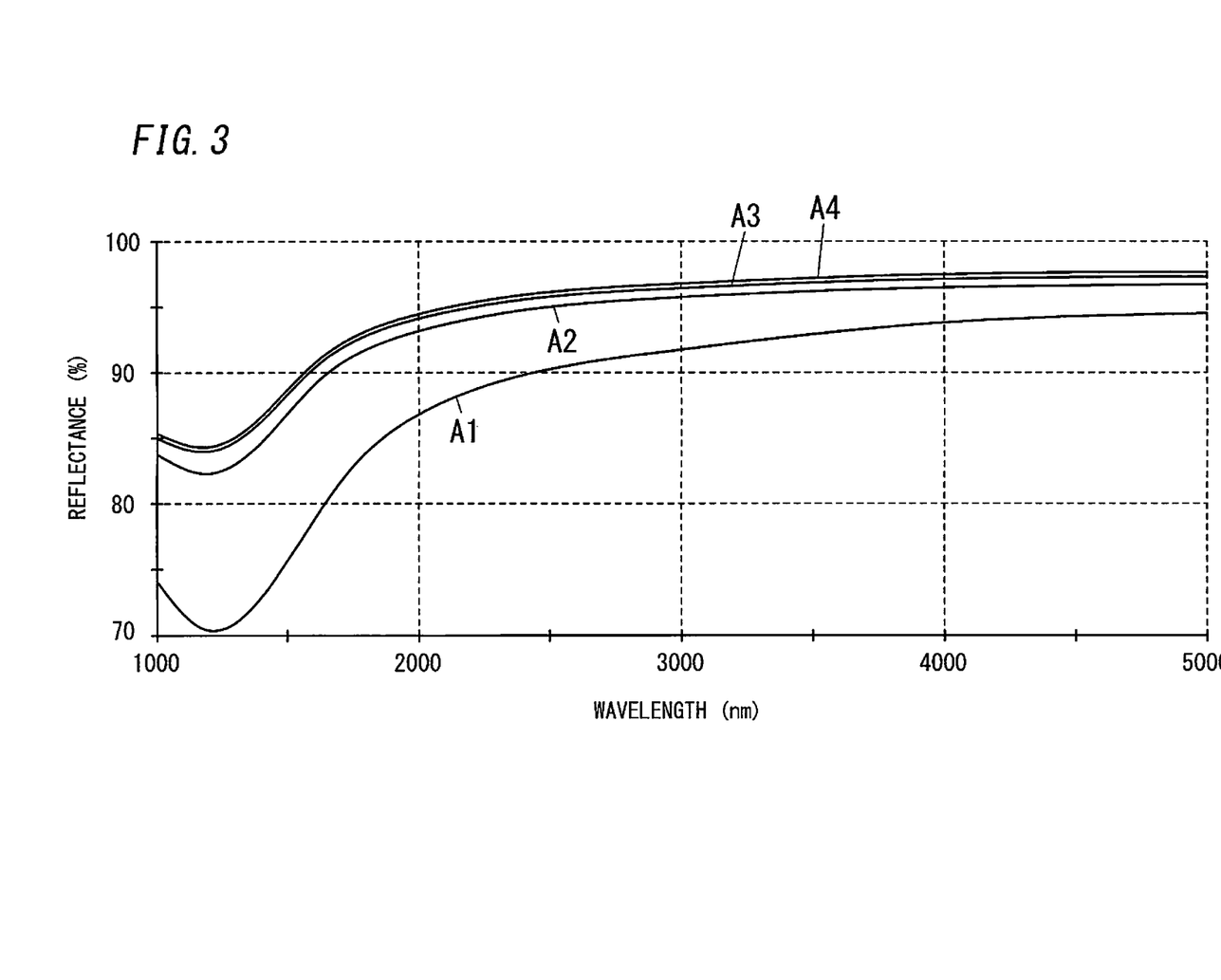
FIG. 3 is a diagram illustrating a relationship between reflectance of a reflecting layer used in the gas sensor according to the embodiment and a wavelength, in which a film thickness of the reflecting layer is varied.
Figure 4:
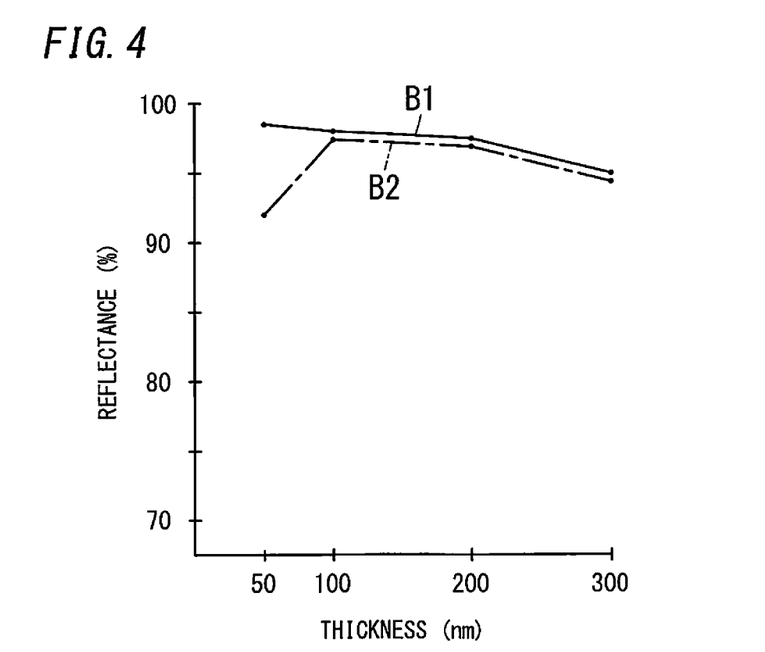
FIG. 4 is a diagram illustrating a degree of lowering of reflectance depending on the film thickness of a corrosion resistant layer used in the gas sensor according to the embodiment.

With respect to the case where, in the optical element 13, the base material 135 is formed by nylon, the reflecting layer 133 is formed by Al, and the corrosion resistant layer 134 is formed by $Al_2O_3$, evaluation results of the relationship between the film thickness and the reflectance of the reflecting layer 133 are shown in FIG. 3, and evaluation results of the relationship between the film thickness and the reflectance of the corrosion resistant layer 134 are shown in FIG. 4.

As shown in FIG. 3, the reflectance of the reflecting layer 133 changes according to the film thickness of the reflecting layer 133 and the wavelength of light that is reflected by the reflecting layer 133. The characteristics A1, A2, A3, and A4 show the cases where the film thickness of the reflecting layer 133 is 40 nm, 60 nm, 80 nm, and 100 nm, respectively. Note that the film thickness of the corrosion resistant layer 134 is 200 nm.

In the case where the detection target gas is carbon dioxide, and the focusing wavelengths are 3.9 μm and 4.3 μm, the reflectance changes little in the range of 60 to 100 nm of the film thickness of the reflecting layer 133, as is clear from FIG. 3. Also, even if the film thickness of the reflecting layer 133 is 40 nm, the reflectance is 90% or more, and accordingly there is no problem in practical use. The reflectance of the reflecting layer 133 is considered to be almost saturated with respect to the focusing wavelengths when the film thickness is 60 nm, and is not affected even if the film thickness is increased. Also, in the case where the film thickness is 40 nm, the reflectance is less than 90% when the wavelength is 2.5 μm or less.

From the above, the film thickness of the reflecting layer 133 needs to be 40 nm or more, practically, and the film thickness is desirably 60 nm or more considering versatility. Note that since the reflectance is not estimated to increase or decrease significantly, even if the film thickness exceeds 100 nm, the upper limit of the film thickness is not defined specifically as long as it is in a range according to which the film formation is relatively easy.

FIG. 4 shows a relationship between the film thickness and the reflectance of the corrosion resistant layer 134. In the present embodiment, since the reflecting layer 133 is covered by the corrosion resistant layer 134, it is predicted that the reflectance will change when the film thickness of the corrosion resistant layer 134 changes. In FIG. 4, the solid line B1 designates the reflectance immediately after film formation, and the dashed-dotted line B2 designates the reflectance after performing endurance test with sulfurous acid. The film thickness of the corrosion resistant layer 134 was set to 50 nm, 100 nm, 200 nm, and 300 nm. The film thickness of the reflecting layer 133 was 150 nm. The relationship shown in FIG. 4 is shown in Table 1. Note that the test condition was that the sample was left for 240 hours in an environment in which the concentration of sulfurous acid was 10 ppm, the temperature was 40° C., the humidity was 95%, and the measurement wavelength of the reflectance was 4000 nm.

TABLE 1

| THICKNESS | REFLECTANCE AT INITIAL STAGE | REFLECTANCE AFTER TEST |
| --- | --- | --- |
| 50 nm | 98.8% | 92.0% |
| 100 nm | 98.5% | 98.3% |
| 200 nm | 98.0% | 97.6% |
| 300 nm | 95.0% | 94.5% |

According to FIG. 4 and Table 1, although the reflectance noticeably decreases after the endurance test in the case where the corrosion resistant layer 134 is 50 nm, in the case where the corrosion resistant layer 134 is 100 nm or more, the reflectance does not change significantly before and after the endurance test. Also, even if the film thickness of the corrosion resistant layer 134 is 50 nm, the reflectance after the endurance test is 90% or more, and it can be said that is in a usable range although it cannot be said that it is good. Also, in a range in which the film thickness of the corrosion resistant layer 134 is 100 to 300 nm, a high reflectance that is substantially 95% or more is obtained both at the initial stage and after the test. Note that the reflectance changes little between the case where the film thickness of the corrosion resistant layer 134 is 100 nm and the case where it is 200 nm, and decreases when the film thickness reaches 300 nm compared with the cases of 100 nm and 200 nm. Note that since the reflectance of almost 95% or more is obtained even if the film thickness is 300 nm, it can be said that the film thickness of 300 nm or less is a desirable condition.

Figure 5:
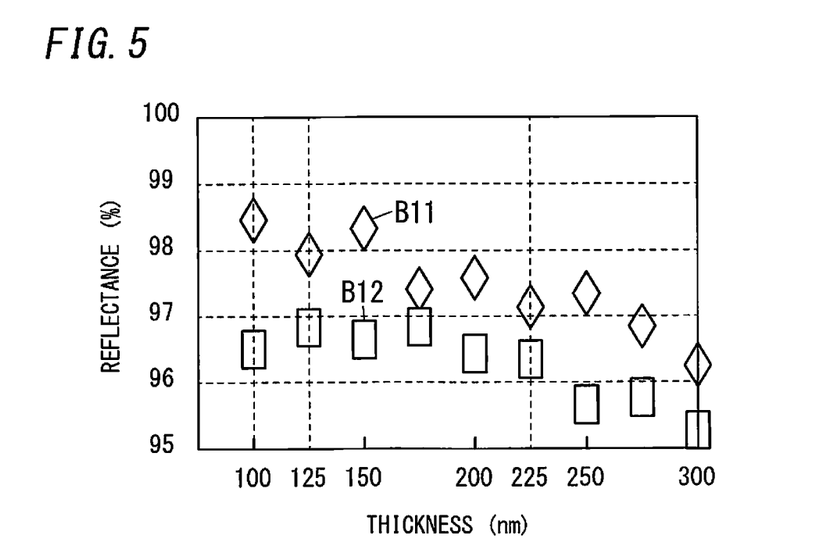
FIG. 5 is a diagram illustrating a degree of lowering of reflectance depending on the film thickness of the corrosion resistant layer used in the gas sensor according to the embodiment.

Also, a relationship between the film thickness and the reflectance of the corrosion resistant layer 134 in a gas sensor formed in a condition that is different from the example in FIG. 4 is shown in FIG. 5. The solid line B11 designates the reflectance immediately after film formation, and the dashed-dotted line B12 designates the reflectance after performing an endurance test with sulfurous acid. The gas sensor having the characteristic in FIG. 5 has a smaller surface roughness compared with the gas sensor having the characteristic in FIG. 4. Note that the smaller the surface roughness is, that is, the smoother the surface is, the higher the reflectance is.

From the above, although the film thickness of 50 nm or more of the corrosion resistant layer 134 satisfies the endurance, the lower limit value of the film thickness is desirably 100 nm, considering the reflectance after a corrosion resistance test. Considering the difference between the reflectance before the corrosion resistance test and the reflectance after the corrosion resistance test, the lower limit value of the film thickness is further desirably 125 nm. Also, the upper limit value of the film thickness is desirably 300 nm. Considering the reflectance after the corrosion resistance test, the upper limit value of the film thickness is further desirably 225 nm, and the upper limit value of the film thickness is furthermore desirably 200 nm.

In the case where the lower limit value of the film thickness is 100 nm, in FIG. 5, since the reflectance before the corrosion resistance test is 98.5%, and the reflectance after the corrosion resistance test is 96.5%, the difference between the reflectance before the corrosion resistance test and the reflectance after the corrosion resistance test is 2%.

On the other hand, in the case where the film thickness is 125 nm or more and 225 nm or less, the difference between the reflectance before the corrosion resistance test and the reflectance after the corrosion resistance test can be made less than 2%. In the case where the film thickness is 150 nm, according to which the reflectance difference is the largest in the range of 125 nm to 225 nm inclusive, since the reflectance before the corrosion resistance test is 98.3% and the reflectance after the corrosion resistance test is 96.6%, the difference between the reflectance before the corrosion resistance test and the reflectance after the corrosion resistance test is 1.7%.

In order to make the reflectance after the endurance test large to some extent and make the difference of the reflectance before the endurance test and the reflectance after the endurance test small to the greatest extent possible, the film thickness of the corrosion resistant layer 134 is desirably 125 nm or more and 225 nm or less. Specifically, in the range of the film thickness of 125 nm to 225 nm inclusive, the reflectance after the corrosion resistance test can be made 96% or more, and the difference between the reflectance before the corrosion resistance test and the reflectance after the corrosion resistance test can be made less than 2%.

That is to say, the condition in the case where the incident light on the light receiving element 12 is in the infrared region (region including wavelength band of 3.9 to 4.3 μm), the reflecting layer 133 is formed by Al, and the corrosion resistant layer 134 is formed by $Al_2O_3$ is as follows. That is, the lower limit value of the film thickness of the reflecting layer 133 is 40 nm, and is desirably 60 nm. Also, the lower limit value of the film thickness of the corrosion resistant layer 134 is 50 nm, and is desirably 100 nm. The lower limit value of the film thickness is more desirably 125 nm. The upper limit value of the film thickness of the corrosion resistant layer 134 is 300 nm, is desirably 225 nm, and is more desirably 200 nm. The film thickness of the corrosion resistant layer 134 is desirably in a range of 125 nm to 225 nm inclusive, considering reduction of degradation of the reflectance during the endurance test.

Note that if the corrosion resistant layer is formed by a synthetic resin as in a conventional example, the corrosion resistant layer may absorb light in the infrared region, and is difficult to apply to an application in which light in the infrared region is used. In contrast, the corrosion resistant layer 134 including $Al_2O_3$ formed by vapor plating does not degrade reflectance of the reflecting layer 133 with respect to light in the infrared region, as in the example described above, and as a result the corrosion resistant layer 134 can be applied to an application in which light in the infrared region is used. Also, in the case where liquid phase plating is performed, different tanks are needed for respective process steps of pretreatment, formation of the reflecting layer, and formation of the corrosion resistant layer. In contrast, in the present embodiment, since the corrosion resistant layer 134 is formed by vapor plating, all the process steps can be performed in the same chamber. Also, although process steps of cleaning and drying are needed between process steps in the liquid phase plating, the vapor plating does not require these process steps, and as a result, the process steps can be simplified.

Hereinafter, a method for forming the reflecting layer 133 and the corrosion resistant layer 134 will be described. The film formation of the reflecting layer 133 and the corrosion resistant layer 134 is performed in a gas phase. Specifically, in the case where the reflecting layer 133 and the corrosion resistant layer 134 are made of the materials described above, the film formation is performed by vapor deposition or sputtering. In the case where other materials are adopted for the reflecting layer 133 and the corrosion resistant layer 134, film formation can be performed also by CVD (Chemical Vapor Deposition). Hereinafter, the term vapor plating is used when vapor deposition, sputtering, and CVD are not distinguished. That is, vapor plating is a collective term including vapor deposition, sputtering, and CVD.

Hereinafter, the formation method of the reflecting layer 133 and the corrosion resistant layer 134 will be described in the case where Al is selected as the material of the reflecting layer 133, and $Al_2O_3$ is selected as the material of the corrosion resistant layer 134. The film formation of the reflecting layer 133 and the corrosion resistant layer 134 is performed before coupling the two half-split bodies 13A and 13B that form the optical element 13. That is, the reflecting layer 133 and the corrosion resistant layer 134 are formed on the base material 135 of each of the half-split bodies 13A and 13B, and thereafter the half-split bodies 13A and 13B are coupled.

The reflecting layer 133 and the corrosion resistant layer 134 are formed by one of the following two methods in the case where the material of the reflecting layer 133 includes Al, and the material of the corrosion resistant layer 134 includes $Al_2O_3$.

A first method includes a process in which the reflecting layer 133 including Al is formed on a portion that is to be the light guide hole 132 in the base material 135 of each of the half-split bodies 13A and 13B by vapor plating, and a process in which, thereafter, the corrosion resistant layer 134 including $Al_2O_3$ is formed on the surface of the reflecting layer 133 by vapor plating. Note that vapor deposition materials need to be changed between forming the reflecting layer 133 and forming the corrosion resistant layer 134, in the case where the film formation method is vapor deposition. Targets need to be changed between forming the reflecting layer 133 and forming the corrosion resistant layer 134, in the case where the film formation method is sputtering.

A second method includes a process in which the reflecting layer 133 is formed on a portion that is to be the light guide hole 132 in the base material 135 of each of the half-split bodies 13A and 13B by vapor plating in a vacuum atmosphere, and a process in which, thereafter, the corrosion resistant layer 134 is formed by vapor plating in an oxidizing atmosphere in which oxygen is introduced. That is, in this method, after forming the reflecting layer 133 in a vacuum atmosphere, the corrosion resistant layer 134 is formed in an oxidizing atmosphere in which oxygen is introduced without changing the vapor deposition material or the target. Accordingly, the corrosion resistant layer 134 is formed by an oxide of the vapor deposition material or the target. Since the material of the reflecting layer 133 is Al, in the present example, the corrosion resistant layer 134 including $Al_2O_3$ can be formed without changing the vapor deposition material or the target.

By adopting the second method, in forming the reflecting layer 133 and the corrosion resistant layer 134, the reflecting layer 133 and the corrosion resistant layer 134 that have different properties can be formed only by changing the atmosphere in film formation without changing the vapor deposition material or the target.

From the above, the second method is advantageous in that operation time needed for the production of the optical element 13 is reduced compared with a case where an operation to change the vapor deposition material or the target is required as in the first method. Also, in the first method, the chamber needs to be depressurized to a vacuum atmosphere every time the vapor deposition material or the target is changed. In contrast, in the second method, the chamber needs to be depressurized only once in order to form the reflecting layer 133 and the corrosion resistant layer 134. That is, the second method is advantageous in that less energy is required for depressurization than the first method.

The condition in implementing the second method will be illustrated. In forming the reflecting layer 133, the inside of the chamber in which the half-split bodies 13A and 13B were placed was depressurized to $1.0 \times 10^{-3}$ Pa to be a vacuum atmosphere. In this vacuum atmosphere, Al was formed on a portion (inner surface) to be the light guide hole 132 in each of the half-split bodies 13A and 13B by vapor deposition. The film formation rate, at this time, was set to 3.0 nm/s, and the reflecting layer 133 having a film thickness of 150 nm was formed. Thereafter, the pressure inside the chamber was adjusted to approximately $3.0 \times 10^{-2}$ Pa by introducing oxygen into the chamber, and the inside of the chamber was put in an oxidizing atmosphere. Vapor deposition of Al was performed again in this oxidizing atmosphere. The film formation rate at this time was set to 0.5 nm/s, and the corrosion resistant layer 134 having a film thickness of 200 nm was finally formed.

The film formation condition for the reflecting layer 133 and the corrosion resistant layer 134 described above is an example, and the pressure inside the chamber, the film formation rate, and the like, in the vacuum atmosphere and in the oxidizing atmosphere, are set appropriately depending on the film thickness and the material of the reflecting layer 133 and the corrosion resistant layer 134.

The optical sensor apparatus (gas sensor) according to the present embodiment includes the light receiving element 12 and the optical element 13. The light receiving element 12 is configured to produce an output according to the light receiving state. The optical element 13 includes the reflecting layer 133 including a metal film, and is arranged such that at least some of the incident light on the light receiving element 12 is light that is reflected by the reflecting layer 133. The optical element 13 further includes the corrosion resistant layer 134 for suppressing corrosion of the reflecting layer 133. The reflecting layer 133 includes the surface covered by the corrosion resistant layer 134 formed by vapor plating.

As with the present embodiment, the optical sensor apparatus (gas sensor) preferably further includes the light emitting element 11. The light emitting element 11 has an emission wavelength that is in the predetermined wavelength region. In this case, the light receiving element 12 is configured such that the received light intensity with respect to the specific wavelength determined by the type of the detection target gas among the wavelength region is reflected in the output value. The optical element 13 is arranged such that the optical path between the light emitting element 11 and the light receiving element 12 is formed in the monitoring space (light guide hole 132) into which the detection target gas is introduced.

As with the optical sensor apparatus (gas sensor) according to the present embodiment, it is preferable that the optical element 13 is tubular and includes: the tube wall having the air holes 131 passing through the tube wall; and the inner surface on which the reflecting layer 133 is disposed. In this case, the light emitting element 11 is coupled to one end portion of the optical element 13 in the specific direction in which the opening surfaces 136 and 137 of the two end portions of the optical element 13 oppose each other. The light receiving element 12 is coupled to another end portion of the optical element 13 in the specific direction. The optical element 13 is configured to guide light between the light emitting element 11 and the light receiving element 12.

As with the optical sensor apparatus (gas sensor) according to the present embodiment, it is preferable that the corrosion resistant layer 134 has a film thickness of 100 nm or more.

As with the optical sensor apparatus (gas sensor) according to the present embodiment, it is more preferable that the corrosion resistant layer 134 has a film thickness of 125 nm or more and 225 nm or less.

As with the optical sensor apparatus (gas sensor) according to the present embodiment, it is preferable that the incident light on the light receiving element 12 is light in the infrared region, the reflecting layer 133 is formed by Al, and the corrosion resistant layer 134 is formed by $Al_2O_3$.

A method of producing the optical element 13 used in the optical sensor apparatus (gas sensor) according to the present embodiment includes a step of forming the reflecting layer 133 by forming Al film in a gas phase on a target surface of the base material 135 of the optical element 13, and forming the corrosion resistant layer 134 including $Al_2O_3$ in a gas phase on a surface of the reflecting layer 133 after forming the reflecting layer 133.

As with the method of producing the optical element 13 used in the optical sensor apparatus (gas sensor) according to the present embodiment, it is preferable that the film formation of the reflecting layer 133 and the film formation of the corrosion resistant layer 134 are performed in the same space, and the film formation of the reflecting layer 133 is performed in a vacuum atmosphere, and the film formation of the corrosion resistant layer 134 is performed in an oxidizing atmosphere in which oxygen is introduced.

Figure 6:
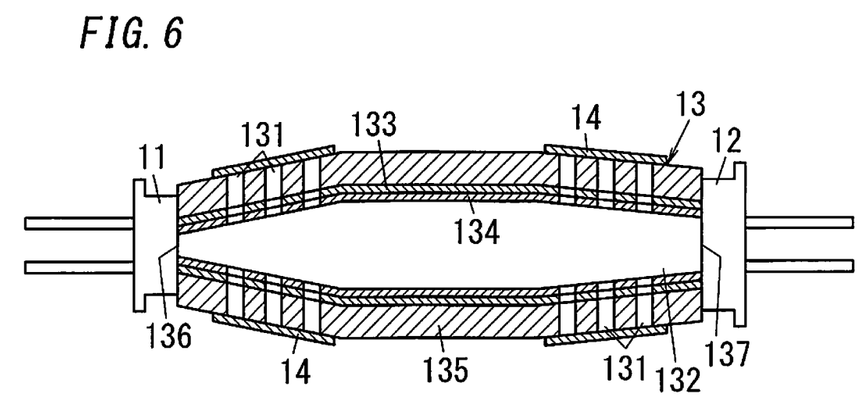
FIG. 6 is a cross-sectional view illustrating a modification of the gas sensor according to the embodiment.

Note that the optical sensor apparatus (gas sensor) according to the present embodiment may further include, as shown in FIG. 6, a plurality of (four in the diagram) filters 14 that are provided on an outer surface of the optical element 13 so as to cover the air holes 131.

The filters 14 cause gas to pass through a plurality of (three in the diagram) the air holes 131, and prevent a solid body and a liquid body from passing through the plurality of air holes 131. The filters 14 are formed by polytetrafluoroethylene or the like, for example. As an example, the filters 14 are formed by Gore-Tex (registered trademark) using polytetrafluoroethylene. It is preferable that the film thickness of each filter 14 is approximately 1 mm.

The filters 14 are adhered to the outer surface of the optical element 13 so as to cover the plurality of air holes 131, for example. As an example, the filters 14 are adhered to the outer surface of the optical element 13 by an adhesive. Since each of the filters 14 is formed in a sheet-like shape, the filters 14 are adhered to the outer surface in a state in which each filter 14 is deformed to the shape of the outer surface of the optical element 13, even though the outer surface of the optical element 13 is a curved surface.

Accordingly, the optical sensor apparatus shown in FIG. 6 can prevent a solid body and a liquid body from penetrating into the light guide hole 132 from the outside via the air holes 131.

Note that the optical sensor apparatus may include one filter instead of the plurality of filters 14. Also, each filter 14 is not limited to being configured to cover a plurality of the air holes 131, and need only be provided on the outer surface of the optical element 13 so as to cover at least one air hole 131.

As with the optical sensor apparatus shown in FIG. 6, each filter 14 is preferably provided in a region that includes at least a portion of the coupling portion of the pair of half-split bodies 13A and 13B, among the outer surface of the optical element 13. In this case, the optical element 13 includes the pair of half-split bodies 13A and 13B. Each of the pair of half-split bodies 13A and 13B includes the reflecting layer 133 and the corrosion resistant layer 134. Recessed portions 138 and 139 for forming the air holes 131 are formed respectively in the half-split bodies 13A and 13B. The half-split bodies 13A and 13B are coupled such that the recessed portions 138 and 139 oppose each other to form the air holes 131. The filters 14 are provided in a region that includes at least a portion of the coupling portion of the pair of half-split bodies 13A and 13B among the outer surface of the optical element 13.

In the optical sensor apparatus shown in FIG. 6, since each filter 14 is provided by adhesion or the like at the coupling portion between the half-split body 13A and the half-split body 13B, the coupling strength between the half-split body 13A and the half-split body 13B can be increased.

Although the present invention has been described with reference to a certain preferred embodiment, numerous modifications and variations can be made by those skilled in the art without departing from the true spirit and scope of this invention, namely claims.

The invention claimed is:

1. An optical sensor apparatus comprising:
a light receiving element configured to produce an output according to a light receiving state;
an optical element comprising a reflecting layer comprising a metal film, and being arranged such that at least some of incident light on the light receiving element is light that is reflected by the reflecting layer;
a light emitting element with an emission wavelength that is in a predetermined wavelength region; and
a filter,
the optical element further comprising a corrosion resistant layer for suppressing corrosion of the reflecting layer,
the reflecting layer comprising a surface covered by the corrosion resistant layer formed by vapor plating,
the light receiving element being configured such that a received light intensity with respect to a specific wavelength determined by a type of a detection target gas among the predetermined wavelength region is reflected in an output value, and
the optical element being arranged such that an optical path between the light emitting element and the light receiving element is formed in a monitoring space into which the detection target gas is introduced,
the optical element being tubular, and comprising: a tube wall having an air hole passing through the tube wall; and an inner surface on which the reflecting layer is disposed,
the light emitting element being coupled to one end portion of the optical element in a specific direction in which opening surfaces of two end portions of the optical element oppose each other,
the light receiving element being coupled to another end portion of the optical element in the specific direction,
the optical element being configured to guide light between the light emitting element and the light receiving element,
the filter being provided on an outer surface of the optical element so as to cover the air hole, and
the filter causing gas to pass through the air hole and preventing at least one of a solid body and a liquid body from passing through the air hole.

2. The optical sensor apparatus according to claim 1, wherein the corrosion resistant layer has a film thickness of 100 nm or more.

3. The optical sensor apparatus according to claim 2, wherein incident light on the light receiving element is light in an infrared region, and
wherein the reflecting layer is formed by Al, and the corrosion resistant layer is formed by $Al_2O_3$.

4. A method of producing an optical element used in the optical sensor apparatus according to claim 3, the method comprising:
forming the reflecting layer by forming Al film in a gas phase on a target surface of a base material of the optical element; and
forming the corrosion resistant layer comprising $Al_2O_3$ in a gas phase on a surface of the reflecting layer after forming the reflecting layer.

5. The optical sensor apparatus according to claim 2, wherein the corrosion resistant layer has a film thickness of 125 nm or more and 225 nm or less.

6. The optical sensor apparatus according to claim 1, wherein incident light on the light receiving element is light in an infrared region, and
wherein the reflecting layer is formed by Al, and the corrosion resistant layer is formed by $Al_2O_3$.

7. A method of producing an optical element used in the optical sensor apparatus according to claim 6, the method comprising:
forming the reflecting layer by forming Al film in a gas phase on a target surface of a base material of the optical element; and
forming the corrosion resistant layer comprising $Al_2O_3$ in a gas phase on a surface of the reflecting layer after forming the reflecting layer.

8. The method of producing the optical element used in the optical sensor apparatus according to claim 7, the method comprising:
performing film formation of the reflecting layer and film formation of the corrosion resistant layer in a same space, and
performing the film formation of the reflecting layer in a vacuum atmosphere, and the film formation of the corrosion resistant layer in an oxidizing atmosphere in which oxygen is introduced.

9. The optical sensor apparatus according to claim 1, wherein
the optical element comprises a pair of half-split bodies each comprising the reflecting layer and the corrosion resistant layer,
recessed portions for forming the air hole are formed in each of the pair of half-split bodies,
the pair of half-split bodies are coupled such that the recessed portions oppose each other to form the air hole, and
the filter is provided in a region that includes at least a portion of the coupling portion of the pair of half-split bodies among the outer surface of the optical element.

* * * * *